United States Patent [19]

Song

[11] Patent Number: 5,411,748
[45] Date of Patent: May 2, 1995

[54] PROSTATE EXTRACT SUPPLEMENTED WITH ZINC

[76] Inventor: Moon K. Song, 10922 Yolanda Ave., Northridge, Calif. 91326

[21] Appl. No.: 179,761

[22] Filed: Jan. 7, 1994

Related U.S. Application Data

[63] Continuation of Ser. No. 964,879, Oct. 22, 1992, abandoned.

[51] Int. Cl.$^6$ .................... A61K 33/30; A61K 35/48
[52] U.S. Cl. .................................. 424/559; 424/643
[58] Field of Search ............... 424/559, 643; 514/560, 514/494

[56] References Cited

U.S. PATENT DOCUMENTS 4,302,447  11/1981  Horrobin .......................... 424/643

FOREIGN PATENT DOCUMENTS 1740004  6/1992  U.S.S.R. .

OTHER PUBLICATIONS

Buxade Vinas, Chem. Abstracts CA107(5):39206z, 1985.
Buxade Vinas, Chem. Abstracts CA107(5):39205y, 1985.
Rossetti et al., Chem. Abstracts CA114(9):75015q, 1990.
Micossi et al., Chem. Abstracts CA91(11):83900w, 1978.
M. K. Song, et al.; Journal of Nutrition; vol. 109, No. 12, Dec. 1979; pp. 2152–2158; "Evidence for an Important Role of Prostaglandins E$_2$ and F$_2$ in the Regulation of Zinc Transport in the Rat".
Moon K. Song, et al.; Comp. Biochem. Physiol., vol. 101A, No. 3, pp. 477–481, 1992; "Prostaglandin Interacts with Steroid Sex Hormones in the Regulation of Intestinal Zinc Transport".
M. K. Song, et al.; Life Sciences, vol. 33, pp. 2399–2408; "A New Low-Molecular-Weight Calcium-Binding Ligand in Rat Small Intestine", 1983.
N. F. Adham, et al.; Nutrition and Metabolism; vol. 24: 281–290 (1980); "Effect of Calcium and Copper on Zinc Absorption in the Rat".
Moon K. Song, et al.; Comp. Biochem. Physiol.; vol. 85C, No. 2, pp. 283–289; 1986; "Relative Zinc-Binding Activities of Ligand in the Cytosol of Rat Small Intestine".
Moon K. Song; Comp. Biochem. Physiol.; vol. 87A, No. 2, pp. 223–230, 1987; "Low-Molecular-Weight Zinc-Binding Ligand: A Regulatory Modulator for Intestinal Zinc Transport".
Moon K. Song, et al.; Biological Trace Element Research; vol. 11, 1986; pp. 75–88; "Levels and Distribution of Zinc, Copper, Magnesium, and Calcium in Rats Fed Different Levels of Dietary Zinc".
M. K. Song., et al.; Biochemical Archives, vol. 1, pp. 75–83; "Metabolic Influences on Intestinal Zinc Uptake in Rats", 1985.
Moon K. Song, et al.; Biological Trace Element Research; vol. 6, 1984; "Metabolism of Zinc-Binding Ligands in Rat Small Intestine", pp. 181–193.
George Y. Luh, et al.; Comp. Biochem. Physiol.; vol. 91B, No. 3, pp. 569–576, 1988; "Characterization of the Low Mol. Wt Zinc-Binding Ligand From Rat Small Intestine by Comparison to the Organic Zinc-Binding Ligands".
S. Arver; Acta Physiol Scand 1982, 116:67–73; "Zinc and zinc ligands in human seminal plasma".
M. Schneir, et al.; Diabetes, vol. 31, May 1982; "Strep- (List continued on next page.)

*Primary Examiner*—Marianne M. Cintins
*Assistant Examiner*—William R. A. Jarvis
*Attorney, Agent, or Firm*—Knobbe Martens Olson & Bear

[57] ABSTRACT

A composition of matter comprising zinc and an extract of animal prostatic tissue provides a convenient source of both fatty acids and zinc for dietary and therapeutic purposes. The pharmaceutical composition is useful for the treatment of diabetes.

7 Claims, No Drawings

OTHER PUBLICATIONS tozotocin-induced Diabetic Rat Enhanced Catabolism of collagen Formed Both Before and During the Diabetic State".

M. Johnson, et al.; The Lancet I: 325–326, 1979; "Vascular Prostacyclin May be Reduced in Diabetes in Man".

K. Engelbart, et al.; Virchows Arch.Abt.B.Zellpath. 4, 294–302 (1970); "Uber das funktionelle Verhalten von Zink und Insulin in den B-Zellen des Rattenpankreas".

J. L. Marx; Science, vol. 225, pp. 1381–1383; Sep. 1984; "Diabetes—A Possible Autoimmune Disease".

L. Hurley, et al.; The Lancet I: 1979; pp. 677–678; "Zinc Citrate, Human Milk and Acrodermatitis Enteropathica".

S. Katayama, et al.; Hypertension Program Unit, vol. 7, No. 4, Jul.–Aug. 1985; pp. 554–561; "Hypertension in Experimental Diabetes Mellitus Renin-Prostaglandin Interaction".

W. T. Johnson, et al.; J. Nutr. 115: 1217–1227, 1985; "Intestinal Absorption and Excretion of Zinc in Streptozotocin-Diabetic Rats as Affected by Dietary Zinc and Protein".

R. P. Robertson, et al.; Journal of Clinical Investigation, vol. 60, Sep. 1977; pp. 747–753; "A Role for Prostaglandin E in Defective Insulin Secretion and Carbohydrate Intolerance in Diabetes Mellitus".

G. W. Evans, et al; J.Nutr. 110:1076–1080, 1980; "Zinc Absorption in Rats Fed a Low-Protein Diet and a Low-Protein Diet Supplemented with Tryptophan or Picolinic Acid".

H. E. Harrison, et al.; Life Sciences, vol. 23, pp. 351–356; "Decreased Vascular Prostacyclin in Experimental Diabetes", 1978.

M. K. Chooi, et al.; Nutr.Metabol.20: 135–142 (1976); "Influence of Age and Sex on Plasma Zinc Levels in Normal and Diabetic Individuals".

Biochemical Medicine 23, pp. 231–235; 1980; *Short Communications*; "Altered Synthesis of Prostaglandins in Platelet and Aorta from Spontaneously Diabetic Wistar Rats".

R. J. Illman, et al.; Atherosclerosis, 59, 1986, pp. 313–321; "Time-Course of Changes in Plasma Lipids in Diabetic Rats Fed Diets High in Fish or Safflower Oils".

A. Reznikvo, et al.; Endocrinologia Experimentalis, vol. 24, 1990; pp. 437–447; "Nonsteroid Antiandrogen Inhibiting Effect on Testosterone Metabolism in Rat Prostate and Liver".

H. E. Harrison, et al.; Diabetologia, 18, pp. 65–68, 1980; "Effect of Insulin Treatment on Prostacyclin in Experimental Diabetes".

G. F. Bottazzo, et al.; Immunology Today, vol. 5, No. 8, 1984, pp. 203–231; "Hypotheses on Genetic Contributions to the Aetiology of Diabetes Mellitus".

D. A. Scott, et al.; Connaught Laboratories, University of Toronto, Toronto, Canada; pp. 725–728; "The Insulin and The Zinc Content of Normal and Diabetic Pancrease", 1938.

B. Koletzko, et al.; Eur.J.Pediatr (1985) 143: 310–314; "Fatty acid composition of plasma lipids in acrodermatitis enteropathica before and after zinc supplementation".

F. K. Ghishan, et al.; Life Sciences, vol. 32, pp. 1735–1741; "Intestinal Transport of Zinc in the Diabetic Rat", 1983.

W. B. Kinlaw, M.D., et al.; The American Journal of Medicine, vol. 75, Aug. 1983, pp. 273–277; "Abnormal Zinc Metabolism in Type II Diabetes Mellitus".

Moon K. Song, Ph.D., et al.; The American Journal of Clinical Nutrition 41; Jun. 1985; pp. 1201–1209; "Relationship between zinc and prostaglandin metabolisms in plasma and small intestine or rats".

M. K. Song, et al.; Life Sciences, vol. 42, pp. 687–695; "Intestinal Zinc Transport: Influence of Streptozotocin-Induced Diabetes, Insulin and Arachidonic Acid", 1988.

R. Paul Robertson, M.D.; Symposium on Prostaglandins; Medical Clinic of North American, vol. 65, No. 4, Jul. 1981; "Prostaglandins, Glucose Homeostasis, and Diabetes Mellitus".

M. K. Song, et al.; Prostaglandins Leukotrienes and Medicine 17: 159–166, 1985; "Effect of Oral Administration on Arachidonic Acid on Prostaglandin and Zinc (List continued on next page.)

OTHER PUBLICATIONS

Metabolism in Plasma and Small Intestine of the Rat".

T. Pham et al., "Factors Affecting Zinc Flux Rates of Rat Intestinal Segments Mounted in Ussing Chambers," *Biochem. Arch.* 7:213–219 (1991).

C. K. Lardinois & G. H. Starich, "Polyunsaturated Fats Enhance Peripheral Glucose Utilization in Rats," *J. Am. Coll. Nutr.* 10:340–345 (1991).

S. Southon et al., "Hexose Transport and Musocal Morphology in the Small Intestine of the Zinc–Deficient Rat," *Br. J. Nutr.* 52:371–380 (1984).

M. Song & N. F. Adham, "Role of Prostaglandin $E_2$ in Zinc Absorption in the Rat," *Am. J. Physiol.* 234:E9-9–105 (1978).

M. K. Song et al., "Evidence for a Role of Prostaglandins in the Regulation of Intestinal Zinc Transport," *Nutr. Rep. Int'l.* 32:71–83 (1985).

D. W. Watkins et al., "Zinc Inhibition of Glucose Uptake in Brush Border Membrane Vesciles from Pig Small Intestine," *Pflugers Arch.* 415:165–171 (1989).

M. K. Song et al., "Influence of Prostaglandins on Unidirectional Zinc Fluxes Across the Small Intestine of the Rat," *Br. J. Nutr.* 59:417–428 (1988).

PROSTATE EXTRACT SUPPLEMENTED WITH ZINC

ACKNOWLEDGEMENT OF GOVERNMENT SUPPORT

This invention was made with Government support, namely, the facilities, equipment, and materials of the Department of Veterans' Affairs. The Government has certain rights in this invention.

This application is a continuation of application Ser. No. 07/964,879, filed Oct. 22, 1992, now abandoned.

BACKGROUND

This invention is directed to compositions and pharmaceutical preparations containing zinc chelated by essential fatty acids.

Diabetes, despite the availability of insulin treatment, remains an extremely serious disease, responsible for many deaths and substantial morbidity in the United States and other developed countries. Although insulin can regulate blood sugar levels in diabetics, the degree of control achieved with insulin is typically insufficient to prevent the occurrence of many sequelae from diabetes. These sequelae can include eye damage, often leading to blindness; circulatory problems; problems with wound healing; and other serious consequences. Therefore, improved treatments for diabetes are urgently required.

It is known that prostaglandins (PGs) bind zinc and regulate intestinal zinc transport (M. K. Song & N. F. Adham, "Role of Prostaglandin $E_2$ in Zinc Absorption in the Rat," *Am. J. Physiol.* 234:E99–E105 (1978)) and that zinc influences prostaglandin synthesis activity in the small intestine and the vascular system of rats (M. K. Song & N. F. Adham, "Relationship Between Zinc and Prostaglandin Metabolisms in Plasma in Small Intestine of Rats," *Am. J. Clin. Nutr.* 41:1201–1209 (1985)). A relationship between zinc and the inhibition of glucose absorption is known (S. Southon et al., "Hexose Transport and Mucosal Morphology in the Small Intestine of the Zinc-Deficient Rat," *Br. J. Nutr.* 52:371–380 (1984)). Essential fatty acids include unsaturated fatty acids that are prostaglandin precursors, and administration of essential fatty acids is believed to be beneficial to diabetics (R. J. Illman et al., *Atherosclerosis* 59:313–321 (1986)).

However, because of the interaction between zinc metabolism and prostaglandin synthesis, administration of unsaturated fatty acids or essential fatty acids alone does not yield an optimum improvement in diabetes. Therefore, there is a need to provide an improved treatment of diabetes and other conditions in which zinc metabolism and fatty acid metabolism play roles by providing a convenient source of both zinc and essential fatty acids.

SUMMARY

A composition of matter comprising crystalline zinc chelated unsaturated fatty acids meets this need by providing a convenient source of both zinc and essential fatty acids for treatment of diabetes and other conditions. Preferably, the unsaturated fatty acids comprise essential fatty acids. The essential fatty acids can comprise fatty acids selected from the group consisting of prostaglandins and prostaglandin precursors. Typically, the essential fatty acids comprise at least one fatty acid selected from the group consisting of linoleic, linolenic, and arachidonic acids.

Another aspect of the present invention is a pharmaceutical composition comprising, in a form administrable to a mammal:

(1) the crystalline zinc chelated unsaturated fatty acids of the present invention;
(2) zinc chloride;
(3) a protein hydrolysate; and
(4) at least one pharmaceutically acceptable excipient.

Preferably, the essential fatty acids, the zinc chloride, and the protein hydrolysate are present in a ratio of about 10:1:5 in the pharmaceutical composition. The pharmaceutical composition can be in tablet form or capsule form; preferably, each tablet or capsule contains about 20 milligrams of zinc, with the essential fatty acids, the zinc chloride, and the protein hydrolysate being present in a ratio of about 10:1:5.

Another aspect of the present invention is a method of treating diabetes comprising administering a pharmaceutical composition according to the present invention to a diabetic mammal in a quantity sufficient to reduce blood glucose concentration in the mammal.

DESCRIPTION

I have discovered that a composition of matter comprising crystalline zinc chelated unsaturated fatty acids, and pharmaceutical compositions comprising the crystalline fatty acids, zinc chloride, and a protein hydrolysate provide both zinc and fatty acids and are useful for treatment of diabetes and other conditions affecting zinc and essential fatty acid metabolism.

I. CRYSTALLINE ZINC CHELATED UNSATURATED FATTY ACIDS

One aspect of the present invention is crystalline zinc chelated unsaturated fatty acids, i.e., crystals in which negatively charged fatty acids are bound by positively charged zinc ions.

Preferably, the unsaturated fatty acids comprise essential fatty acids. The essential fatty acids preferably are selected from the group consisting of prostaglandins and prostaglandin precursors. These fatty acids can be obtained from animal prostates, such as cow, sheep, or goat by resuspending the prostates in a buffered aqueous solution, extracting the saturated fatty acids with a highly non-polar organic solvent such as petroleum ether or hexane, extracting unsaturated fatty acids with a more polar organic solvent such as ethyl acetate or chloroform, and then adding zinc chloride in a quantity sufficient to chelate the fatty acids present. Further details of the extraction procedure are given in Example 1, below.

Typically, such essential fatty acids include at least one fatty acid selected from the group consisting of linoleic, linolenic, and arachidonic acid, which are unsaturated fatty acids that are precursors to prostaglandins.

II. PHARMACEUTICAL COMPOSITIONS

Another aspect of the present invention is pharmaceutical compositions. Pharmaceutical compositions according to the present invention contain: (1) essential fatty acids as disclosed above; (2) zinc chloride; (3) protein hydrolysate; and (4) at least one pharmaceutically acceptable excipient.

The protein hydrolysate may be in the form of amino acids or incompletely hydrolyzed protein such as proteoses, peptones, or other partially hydrolyzed proteins, such as casein or albumin.

Preferably, pharmaceutical compositions according to the present invention contain essential fatty acids, zinc chloride, and protein hydrolysate in a ratio of about 10:1:5 by weight. The pharmaceutical compositions can be packaged in tablet or capsule form by procedures well-known in the pharmaceutical art. Preferably, each tablet or capsule contains about 200 mg of essential fatty acids, about 20 mg of zinc, and about 100 mg of protein hydrolysate, in addition to the pharmaceutically acceptable excipient or excipients. Suitable pharmaceutically acceptable excipients for tablets and capsules include inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc. The coating of the capsules can be gelatin or a soluble polymer, as is well-understood in the art. The tablets or capsules are suitable for oral administration.

The pharmaceutical compositions are useful for the treatment of diabetes, hypertension, impotence, and other diseases in which zinc or prostaglandin metabolism is impaired. In particular, diabetes can be treated by administering a pharmaceutical composition according to the present invention to a diabetic mammal in a quantity sufficient to reduce blood glucose concentration in the mammal. Typical doses for patients with diabetes or hypertension, stated as the quantity of zinc, are from about 80 mg to about 300 mg of zinc. These doses can be adjusted by one of ordinary skill in the art according to such factors as the weight, age, sex, and state of health of the patient, as well as according to the response to a particular dosage.

EXAMPLES

EXAMPLE 1

Preparation of Crystalline Zinc Chelated Unsaturated Fatty Acids

Prostates from a cow or goat were obtained from a slaughterhouse, frozen at 70° C. and minced into small pieces. The sliced tissue was suspended in a 10-fold excess (w/v) of 5.0 mM Tris-HCl buffer, pH 8.0, homogenized with a homogenizer such as a Virtis-45 homogenizer (Virtis Co., Gardner, N.Y.), and centrifuged at 4° C. for 20 minutes at 3000 xg. The upper part of the fat was removed physically, and the supernatant was incubated at 37° C. for one hour. The saturated fatty acids were extracted with petroleum ether. The aqueous solution remaining, including the unsaturated fatty acids, was acidified to pH 3.0 with 0.2 N HCl, and the unsaturated fatty acid mixture including prostaglandins was extracted 2 to 3 times with one volume each time of ethyl acetate or chloroform. The ethyl acetate or chloroform extracts were combined. The unsaturated fatty acid solutions were freeze-dried to dryness or evaporated under vacuum. The product at this stage was unsaturated fatty acids in an oil. Then 200 mg of the extract was mixed with 40 mg zinc chloride and 100 mg protein hydrolysate to form a preparation of zinc chelated unsaturated fatty acids.

EXAMPLE 2

Effect of Dietary Zinc on the Survival Rate of Diabetic Rats

Fifty-one rats were divided into three groups of 17 rats each. All of the rats were made diabetic by injection of streptozotocin. One week later, the rats were fed diets with defined quantities of zinc. The first group of 17 rats was fed a zinc-deficient diet with 1 $\mu$g Zn/g, the second group of 17 rats was fed a zinc-adequate diet (37.5 $\mu$g Zn/g), and the third group of 17 rats a zinc-excess diet (1 mg Zn/g). Twenty-five days later, the number of surviving rats was counted. Only 8 out of 17 rats in the zinc-deficient group survived while 11 out of 17 rats in the zinc-adequate group and 15 out of 17 rats in the zinc-excess group survived. Glucose concentration in the tissues of these rats is shown in Table 1. This data clearly indicates that an increase in dietary zinc enhances survival in diabetic rats and reduces the level of glucose present in the tissues of such rats. Because many diabetes complications are believed due to the presence of excess glucose in tissues, these results emphasize that an adequate zinc supply is important in preventing sequelae of diabetes.

TABLE I

GLUCOSE CONCENTRATIONS IN TISSUES OF DIABETIC RATS FED DIETS WITH DIFFERENT CONCENTRATIONS OF ZINC

| Organ | Glucose Concentration | | |
|---|---|---|---|
| | Zinc-Deficient (1 $\mu$g Zn/g) | Zinc-Adequate (37.5 $\mu$g Zn/g) | Zinc-Excess (1 mg Zn/g) |
| Heart[a] | 5.54 | 1.17 | 0.95 |
| Lung[a] | 1.59 | 1.28 | 0.86 |
| Liver[a] | 8.39 | 5.20 | 5.54 |
| Pancreas[a] | 1.20 | 0.82 | 0.96 |
| Spleen[a] | 1.01 | 0.72 | 0.62 |
| Kidney[a] | 2.54 | 1.79 | 1.52 |
| Muscle[a] | 6.52 | 2.37 | 2.20 |
| Small Intestine[a] | 2.54 | 1.48 | 1.38 |
| Colon[a] | 3.18 | 3.05 | 2.81 |
| Skin[a] | 4.91 | 3.81 | 3.33 |
| Plasma[b] | 158 | 156 | 162 |

[a]mg glucose/mg protein
[b]mg glucose/mg plasma

ADVANTAGES OF THE INVENTION

The present invention provides compositions that are a convenient source of both zinc and essential fatty acids as a dietary supplement or treatment for diabetes or other conditions. Because the metabolism of zinc and the metabolism of essential fatty acids, including prostaglandin precursors, are interlinked, the use of such compositions is more effective than is the use of either zinc or fatty acids alone in treating diabetes.

Although the present invention has been described in considerable detail, with reference to certain preferred versions thereof, other versions are possible. Therefore, the spirit and scope of the appended claims should not be limited to the description of the preferred versions contained herein.

I claim:

1. A composition of matter comprising zinc and extract of animal prostatic tissue, said tissue comprising a first group of molecules soluble in a first solvent which is a non-polar solvent having less polarity or the same polarity as petroleum ether or hexane, and also comprising a second group of molecules substantially insoluble in the first solvent, said extract being obtained by a process comprising:

(a) extracting the first group of molecules from the tissue in the first solvent;

(b) discarding the first solvent containing the first group of molecules;

(c) extracting said second group of molecules in a second solvent more polar than the first solvent; and (d) removing the second solvent to create said extract.

2. A pharmaceutical composition comprising, in a form administrable to a mammal:

(a) a composition according to claim 1; and (b) at least one pharmaceutically acceptable excipient.

3. The pharmaceutical composition of claim 2 in tablet form.

4. The pharmaceutical composition of claim 3 wherein each tablet contains about 20 milligrams of zinc.

5. The pharmaceutical composition of claim 2 in capsule form.

6. The pharmaceutical composition of claim 2 wherein said composition contains from about 20 milligrams of zinc to about 300 milligrams of zinc.

7. A method of treating diabetes in a diabetic mammal comprising administering the composition of claim 2 to said diabetic mammal in a quantity sufficient to reduce blood glucose concentration in the mammal.

* * * * *